US010024852B2

(12) United States Patent
Gunn et al.

(10) Patent No.: US 10,024,852 B2
(45) Date of Patent: *Jul. 17, 2018

(54) USE OF DISULFIDE BONDS TO FORM A REVERSIBLE AND REUSABLE COATING FOR NANOFLUIDIC DEVICES (71) Applicant: International Business Machines Corporation, Armonk, NY (US)

(72) Inventors: Natalie Gunn, Victoria (AU); Jose M. Lobez Comeras, New York, NY (US); Priscilla Rogers, Fitzroy (AU); John Wagner, Carlton (AU)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 817 days.

This patent is subject to a terminal disclaimer.

(21) Appl. No.: 14/070,985

(22) Filed: Nov. 4, 2013

(65) Prior Publication Data
US 2015/0104877 A1 Apr. 16, 2015

Related U.S. Application Data (63) Continuation of application No. 14/053,956, filed on Oct. 15, 2013.

(51) Int. Cl.
*G01N 33/543* (2006.01)
*G01N 33/487* (2006.01)

(52) U.S. Cl.
CPC .. *G01N 33/54393* (2013.01); *G01N 33/48721* (2013.01); *G01N 33/54306* (2013.01); *Y10T 436/143333* (2015.01)

(58) Field of Classification Search
CPC ....... G01N 33/48721; G01N 33/54306; G01N 33/54393; Y10T 436/143333
See application file for complete search history.

(56) References Cited

U.S. PATENT DOCUMENTS

| | | | |
|---|---|---|---|
| 5,395,587 A * | 3/1995 | Brigham-Burke . | G01N 35/1095 422/502 |
| 5,397,695 A | 3/1995 | Sutton et al. | |
| 5,942,443 A | 8/1999 | Parce et al. | |
| 6,428,959 B1 | 8/2002 | Deamer | |
| 6,627,067 B1 | 9/2003 | Branton et al. | |
| 7,459,066 B2 | 12/2008 | Broadley et al. | |
| 7,625,469 B1 | 12/2009 | Yelton et al. | |
| 7,846,656 B2 | 12/2010 | Mirzabekov et al. | |
| 8,105,471 B1 | 1/2012 | Han et al. | |
| 8,232,105 B1 | 7/2012 | Scott | |
| 8,247,238 B2 | 8/2012 | Meinhart et al. | |
| 8,262,879 B2 | 9/2012 | Oliver | |
| 8,278,055 B2 | 10/2012 | Su et al. | |
| 8,388,908 B2 | 3/2013 | Blaga et al. | |
| 8,481,334 B1 | 7/2013 | Saul | |
| 8,835,362 B2 | 9/2014 | Downtown et al. | |
| 8,906,609 B1 | 12/2014 | Smirnov et al. | |
| 9,255,321 B2 * | 2/2016 | Baldauf | ............. C23C 14/12 |
| 9,297,062 B2 * | 3/2016 | Baldauf | ............. C23C 14/12 |
| 9,303,310 B2 * | 4/2016 | Baldauf | ............. C23C 14/22 |
| 9,309,590 B2 * | 4/2016 | Baldauf | ............. C23C 14/22 |
| 2003/0040173 A1 | 2/2003 | Fonash et al. | |
| 2004/0144658 A1 | 7/2004 | Flory | |
| 2004/0147045 A1 * | 7/2004 | Nelson | ............. G01N 33/543 436/518 |
| 2004/0202994 A1 | 10/2004 | Timperman | |
| 2005/0221333 A1 | 10/2005 | Sundararajan et al. | |
| 2006/0019247 A1 | 1/2006 | Su et al. | |
| 2006/0231419 A1 | 10/2006 | Barth et al. | |
| 2006/0275778 A1 | 12/2006 | Wu et al. | |
| 2007/0138132 A1 | 6/2007 | Barth | |
| 2008/0003571 A1 | 1/2008 | McKernan et al. | |
| 2008/0067056 A1 | 3/2008 | Searson et al. | |
| 2008/0073512 A1 | 3/2008 | Siuzdak et al. | |
| 2009/0136948 A1 | 5/2009 | Han et al. | |
| 2009/0305273 A1 | 12/2009 | Cao et al. | |
| 2010/0009872 A1 | 1/2010 | Eid et al. | |
| 2010/0151454 A1 | 6/2010 | Sundararajan et al. | |
| 2011/0053284 A1 | 3/2011 | Meller et al. | |
| 2011/0168562 A1 | 7/2011 | Nuckolls et al. | |
| 2012/0088315 A1 | 4/2012 | Merelle et al. | |
| 2012/0193231 A1 | 8/2012 | Afzali-Ardakani et al. | |

(Continued)

FOREIGN PATENT DOCUMENTS

WO 01027610 A3 4/2001
WO WO 2012/142174 * 10/2012

OTHER PUBLICATIONS

Batista-Viera et al., "A new method for reversible immobilization of thiol biomolecules based on solid-phase bound thiolsulfonate groups," Appl. Biochem. Biotechnol., 1991, vol. 31, issue 2, pp. 175-195.*
Smith et al., "Formation, Spectroscopic Characterization, and Application of Sulfhydryl-Terminated Alkanethiol Monolayers for the Chemical Attachment of DNA onto Gold Surfaces," Langmuir, 2001, vol. 17, No. 8, pp. 2502-2507.*
Danelon, Christophe, et al.; "Fabrication and Functionalization of Nanochannels by Electron-Beam-Induced Silicon Oxide Deposition"; Langmuir; vol. 22; p. 10711-10715; 2006.
Hou, Xu, et al.; "Building Bio-Inspired Artificial Functional Nanochannels: From Symmetric to Asymmetric Modification"; Angew. Chem. Int. Ed.; vol. 51; p. 5296-5307; 2012.
International Search Report and Written Opinion dated Dec. 18, 2014 for Application No. PCT/US2014/052481.

(Continued)

*Primary Examiner* — Galina Yakovleva
(74) *Attorney, Agent, or Firm* — Cantor Colburn LLP; Louis Percello (57) ABSTRACT

A reusable coating for a nanopore structure is disclosed herein. A nanopore structure includes a substrate comprising a nanochannel and a monolayer of a chemical compound disposed onto at least a portion of a surface of the nanochannel. The chemical compound forms a reversible bond with at least one analyte binding compound introduced into the nanochannel. Methods for making and using the reusable coating are also disclosed.

6 Claims, 6 Drawing Sheets

(56) References Cited

U.S. PATENT DOCUMENTS

| | | |
|---|---|---|
| 2012/0222958 A1 | 9/2012 | Pourmand et al. |
| 2012/0256281 A1 | 10/2012 | Harrer et al. |
| 2013/0085680 A1 | 4/2013 | Arlen et al. |
| 2013/0256137 A1 | 10/2013 | Holt |
| 2014/0045270 A1 | 2/2014 | Shim et al. |
| 2014/0106472 A1 | 4/2014 | Ervin et al. |
| 2014/0179540 A1 | 6/2014 | Downtown et al. |
| 2014/0206101 A1 | 7/2014 | Liu et al. |
| 2015/0104352 A1* | 4/2015 | Gunn ............... G01N 33/54306 422/69 |
| 2015/0225838 A1* | 8/2015 | Baldauf ................. C23C 14/12 427/596 |

OTHER PUBLICATIONS

International Search Report and Written Opinion dated Dec. 29, 2014 for Application No. PCT/US2014/058531.
International Search Report and Written Opinion dated Jan. 22, 2015 for Application No. PCT/US2014/50644.
I. Braslavsky, et al., "Sequence Information Can Be Obtained From Single DNA Molecules," Department of Applied Physics, California Institute of Technology; PNAS Apr. 1, 2003; vol. 100; No. 7; pp. 3960-3964.
D. Branton, et al., "The Potential and Challenges of Nanopore Sequencing," Nature Biotechnology; 2008 Nature Publishing Group; pp. 1146-1153.
F. Collins, et al., "The Human Genome Project: Lessons from Large-Scale Biology," Apr. 11, 2003 vol. 300 Science www.sciencemag.org; pp. 286-290.
M. Fedurco, et al., "BTA, a Novel Reagent for DNA Attachment on Glass and Efficient Generation of Solid-Phase Amplified DNA Colonies," Nucleic Acids Research, 2006, vol. 34, No. 3; Published online Feb. 9, 2006; pp. 1-13.
S. Harrer, et al., "Electrochemical Characterization of Thin Film Electrodes Toward Developing a DNA Transistor," Langmuir Article 2010 American Chemical Society; Langmuir 2010, 26(24), pp. 19191-19198.
Harrer, S., et al., "Electrochemical Protection of Thin Film Electrodes in Solid State Nanopores," Nanotechnology 22(2011) 275304 (6pp).
T. Harris, et al., "Single-Molecule DNA Sequencing of a Viral Genome," Science vol. 320, 106 (2008); pp. 106-109.
J. Kasianowicz, et al., "Characterization of Individual Polynucleotide Molecules Using a Membrane Channel," Proc. Natl. Acad. Sci. USA; vol. 93; pp. 13770-13773; Nov. 1996 Biophysics.
B. Luan, et al., "Tribological Effects on DNA Translocation in a Nanochannel Coated with a Self-Assembled Monolayer," J. Phys. Chem B., 2010, 114, pp. 17172-17176.
B. Luan, et al., "Base-by-Base Ratcheting of Single Stranded DNA Through a Solid-State Nanopore," Physical Review Letters 104, 238103 (2010); pp. 238103-1-238103-4.
B. Luan, et al., "Control and Reversal of the Electrophoretic Force on DNA in a Charged Nanopore," J. Phys.: Condens. Matter 22 (2010) 454123 (5pp).
M. Margulies, et al., "Genome Sequencing in Microfabricated High-Density Picolitre Reactors," Nature vol. 437; Sep. 15, 2005 pp. 376-380.
S. Polonsky, et al., "Nanopore in Metal-Dielectric Sandwich for DNA Position Control," Applied Physics Letters 91, 153103 (2007); pp. 153103-1-153103-3.
F. Sanger, et al., "DNA Sequencing with Chain-Terminating Inhibitors," Proc. Natl. Acad. Sci. USA; vol. 74, No. 12; pp. 5463-5467; Dec. 1977 Biochemistry.
D. Scott, et al., "Direct Molecular Evolution of Detergent-Stable G Protein-Coupled Using Polymers Encapsulated Cells," 2012 Elsevier Ltd., J. Mol. Biol. (2013) 425, pp. 662-677.
J. Shendure, et al., "Accurate Multiplex Polony Sequencing of an Evolved Bacterial Genome," Science 309, 1728 (2005); pp. 1728-1732.
G. Turcatti, et al., "A New Class of Cleavable Fluorescent Nucleotides: Synthesis and Optimization as Reversible Terminators for DNA Sequencing by Synthesis," Nucleic Acids Research, 2008, vol. 36, No. 4; Published online Feb. 7, 2008; pp. 1-13.
D. Wang, et al., "DNA-Translocation Through a Solid State Nanopore coated with a Functionally Switchable Self-Assembled Monolayer," IBM T. J. Watson Research Center, Yorktown Heights, NY USA; 2012; pp. 1-18.
E. Yusko, et al., "Developing Nanopores with Fluid Walls for Improved, Single-Molecule Biosensors," Abstract only Feb. 2012; 1 page.
Bayley, Hagan et al.; Stochastic Sensors Inspired by Biology; Nature; vol. 413; p. 226-230; Sep. 13, 2001.
Hickman, James J., et al.; "Toward Orthogonal Self-Assembly of Redox Active Molecules on Pt and Au: Selective Reaction of Disulfide with Au and Isocyanide with Pt"; Langmuir; vol. 8; 357-359; 1992.
Li, Zhiyong, et al.; "Self-Assembly of Alkanethiol Molecules onto Platinum and Platinum Oxide Surfaces"; Langmuir; vol. 19; p. 6744-6749; 2003.
Martin, Benjamin R., et al; "Orthogonal Self-Assembly on Colloidal Gold-Platinum Nanorods"; Advanced Materials; vol. 11, No. 12; p. 1021-1025; 1999.
Miles, Benjamin N., et al.; "Single Molecule Sensing with Solid-State Nanopores: Novel Materials, Methods, and Applications"; Chemical Society Reviews; vol. 42; No. 1; p. 15-28; Jan. 7, 2013.
Petrovykh, Dmitri Y., et al.; Alkanethiols on Platinum: Multicomponent Self-Assembled Monolayers; Langmuir; vol. 22; p. 2578-2587; 2006.
Raillon, C., et al.; "Fast and Automatic Processing of Multi-Level Events in Nanopore Translocation Experiments"; Nanoscale; vol. 4; p. 4916-4924; 2012.
Randolph, S. J., et al.; "Focused, Nanoscale Electron-Beam-Induced Deposition and Etching"; Critical Reviews in Solid State and Materials Sciences; vol. 31; p. 55-89; 2006.
Schoch et al., "Transport Phenomena in Nanofluidics," Reviews of Modern Physics, vol. 80, Jul.-Sep. 2008, 45 pages.
Tabard-Cossa, Vincent, et al.; "Noise Analysis and Reduction in Solid-State Nanopores"; Nanotechnology; vol. 18; p. 1-7; 2007.
Wei, Ruoshan, et al.; "Stochastic Sensing of Proteins with Receptor-Modified Solid-State Nanopores" Nature Nanotechnology; vol. 7; p. 257-263; Apr. 2012.
Liu, Changlu, et al.; "Relaxin-3/Insulin-Like Peptide 5 Chimeric Peptide, a Selective Ligand for G Protein-Coupled Receptor (GPCR)135 and GPCR142 over Leucine-Rich Repeat-Containing G Protein-Coupled Receptor 7"; Molecular Pharmacology; vol. 67, No. 1; p. 231-240; 2005.
Sexton, Lindsay, et al., "Resistive-Pulse Studies of Proteins and Protein/Antibody Complexes Using a Conical Nanotube Sensor," Journal of the American Chemical Society; vol. 129, (2007), pp. 13144-13152.
Waller, A., et al., "High Trhoughput Screening of G-Protein Coupled Receptors via Flow Cytometry," Combinatorial Chemistry & High Throughput Screening; vol. 6 (2003), pp. 389-397.
D. Wang, et al., "Regulating the Transport of DNA through Biofriendly Nanochannels in a Thin Solid Membrane," IBM Research at T.J. Watson Center, Yorktown Heights, NY USA; Published Feb. 5, 2014; pp. 1-6.
D. Wang, et al. "Regulating the Transport of DNA through Biofriendly Nanochannels in a Thin Solid Membrane," IBM Research at T.J. Watson Center, Yorktown Heights, NY USA;Feb. 5, 2014, pp. 1-23.
Martins S.A.M., et al. "Towards the miniaturization of GPCR-based live-cell screening assays";Trends in Biotechnology. 30(11):566-574. Nov. 2012. Available online at—doi:10.1016/j.tibtech.2012.07004.
Maynard JA, et al. Biotechnol J. 4(11):1542-1558. Nov. 2009. Available online at—doi:10.1002/biot.200900195.
Pavlovic "Spatially Controlled Covalent Immobilization of Biomolecules on Silicon Surfaces"; Dissertation, Uppsala University; 2003, 4 pages.

(56) References Cited

OTHER PUBLICATIONS

W. Sparreboom, et al. "Principles and applications of nanofluidic transport," Nature Nanotechnology, vol. 4, No. 11, Nov. 8, 2009, pp. 713-720.

* cited by examiner

USE OF DISULFIDE BONDS TO FORM A REVERSIBLE AND REUSABLE COATING FOR NANOFLUIDIC DEVICES

CROSS-REFERENCE TO RELATED APPLICATIONS AND PRIORITY CLAIM

This application is a continuation of and claims priority from U.S. patent application Ser. No. 14/053,956, filed on Oct. 15, 2013, entitled "USE OF DISULFIDE BONDS TO FORM A REVERSIBLE AND REUSABLE COATING FOR NANOFLUIDIC DEVICES", the entire contents of which are incorporated herein by reference.

BACKGROUND

The present invention relates to nanopores, and more specifically, to nanopore coatings.

Nanopores having nanometer dimensions can provide information on the chemical nature of analytes, e.g., deoxyribonucleic acid (DNA), proteins, and other biomolecules. Solid-state nanopore devices can include a substrate, or membrane, having at least a single aperture, "nanopore," or "nanochannel," which separates the cis and trans chambers, which are filled with an electrolyte solution. The particular dimensions and compositions of nanopore structures and devices are tailored to the desired application.

In operation, an electrical potential difference is generated between the electrolyte solutions separated by the substrate containing the pore by applying a voltage, and the ionic current through the nanopore is measured. Subsequently, passage of analytes through the nanopore induces fluctuations in the measured open pore current level. A detected fluctuation, or a change in detected signal, indicates passage of one or more single molecules of an analyte through the nanopore, which can also be referred to as a translocation event. Alternatively, the molecule may either remain within the nanopore due to a binding event resulting in a sustained change in the signal. When the analyte binds and then leaves the nanopore, the signal then returns to the open pore current level, which is a translocation event.

Translocation and receptor-analyte binding data within the nanochannel can reveal properties about analytes. Indirect measurement techniques of binding of the analyte to a receptor site inside the nanochannel, such as electrical methods described above, can provide valuable information about the chemical and biological nature of many small chemical and biochemical compounds. The inner surface of nanochannels can include coatings, or functional layers, which can be chosen or configured to interact with a predetermined analyte of interest during translocation through the nanochannel.

SUMMARY

According to one embodiment, a nanopore structure comprises a substrate comprising a nanochannel and a monolayer of a chemical compound disposed onto at least a portion of a surface of the nanochannel. The chemical compound forms a reversible bond with at least one analyte binding compound introduced into the nanochannel.

In another embodiment, a method for using a re-usable coating within a nanopore structure comprises forming a monolayer of a chemical compound on a surface of a nanochannel within the nanopore structure; reacting an analyte binding compound with the chemical compound of the monolayer to form a reversible bond, wherein the analyte binding compound comprises a functional group forming the reversible bond and an analyte binding group; measuring one or more electrical signals for an event, the event being a translocation event, a binding event, or both the translocation event and the binding event; severing the reversible bond; and flushing the analyte binding compound from the nanochannel.

Yet in another embodiment, a method for making a reversible analyte-binding coating in a nanopore structure comprises coating a surface of a nanochannel with a chemical compound comprising an initial reactive functional group; disposing an analyte binding compound onto a surface of the nanochannel to form a reversible bond with the reactive functional group, the analyte binding compound comprising an analyte binding group; introducing an analyte into the nanochannel, wherein the analyte binds the analyte binding group; and introducing a severing agent into the nanochannel to reform the initial reactive functional group coating the nanopore.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter, which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Disclosed herein is a method for using reversible bonds to reversibly coat the surface of a nanochannel within a nanopore structure and/or nanopore device. Both nanopore structures including the coating and methods for making and using the coating are disclosed. In one exemplary embodiment, the reversible bonds are disulfide bonds, which are covalent bonds formed between two sulfur atoms.

As used herein, the term "analyte" means a compound, molecule, substance, chemical constituent, or biomolecule that is undergoing analysis or sought to be detected. It is not intended that the present disclosure be limited to a particular analyte. Representative analytes include ions, saccharides, proteins, nucleic acids and nucleic acid sequences.

As used herein, the term "nanopore" means structures having a substrate and a "nanochannel," or a nanoscale passageway through the substrate, through which ionic current can flow. The inner diameter of the nanopore can vary considerably depending on the intended use.

As used herein, the term "nanopore device" means a nanopore separating two fluid reservoirs. In operation, the two fluid reservoirs, cis and trans, are filled with aqueous solutions comprising charged ions, electrolytes, and/or analytes of interest. The charged ions, electrolytes and/or analytes pass between the fluid reservoirs through the nanochannel, which is driven by either concentration gradients or an applied electric field.

As used herein, the term "reversible bond" means any chemical bond that can be broken, severed, cleaved, or reversed by suitable analytical methods known in the art. The terms breaking, cleaving, severing, and like terms are used interchangeably.

As used herein, the terms "sulfhydryl," "thio," and "thiol" mean sulfur-containing functional groups. Sulfhydryl and thiol functional groups include the —SH moiety. Sulfhydryl and thiol functional groups are reactive and can be oxidized to form a disulfide bond.

As used herein, the terms "disulfide" and "disulfide bond" mean the structural unit composed of a linked pair of sulfur atoms. In particular, two sulfhydryl groups combine to form an —S—S— bond. Such disulfide linkages can be broken with reducing agents, which then re-form the original sulfhydryl groups.

As used herein, the term "reducing agent" means any element, compound, or combination of elements and/or compounds that reduces or breaks a disulfide bond.

As used herein, the terms "ligand" and "analyte binding group" are used interchangeably. The term ligand and analyte binding group mean any molecule or functional group that is known or suspected to associate with another molecule or analyte. The terms ligand and analyte binding group encompass inhibitors, activators, agonists, antagonists, natural substrates, analogs of natural substrates, antibodies, chemical compounds, chemical functional groups, or any combination thereof.

As used herein, the term "monolayer" means a layer that is substantially one molecule thick, one atom thick, or one layer thick. Although substantially one layer thick, some variation on the order of zero to two molecules is within the scope of the disclosed embodiments.

A nanopore device is a device with two fluidic reservoirs separated by a nanopore structure. The nanopore structure includes substrate or membrane, e.g., a silica nitride membrane, comprising a nanochannel extending through the substrate and connecting the two fluid reservoirs. The nanochannel is a channel of nanometer scale or larger diameter, which can be drilled through the substrate using transmission electron microscopy (TEM), for example. Nanopore substrates can include more than one nanochannel for parallel analysis.

The nanochannel and fluidic reservoirs can be filled with an aqueous electrolyte solution including charged ions (buffers) and/or other analytes that pass between the two fluid reservoirs through the nanochannel. The charged ions and/or analytes can be driven, for example, by concentration gradients or an applied electric field.

Figure 1:
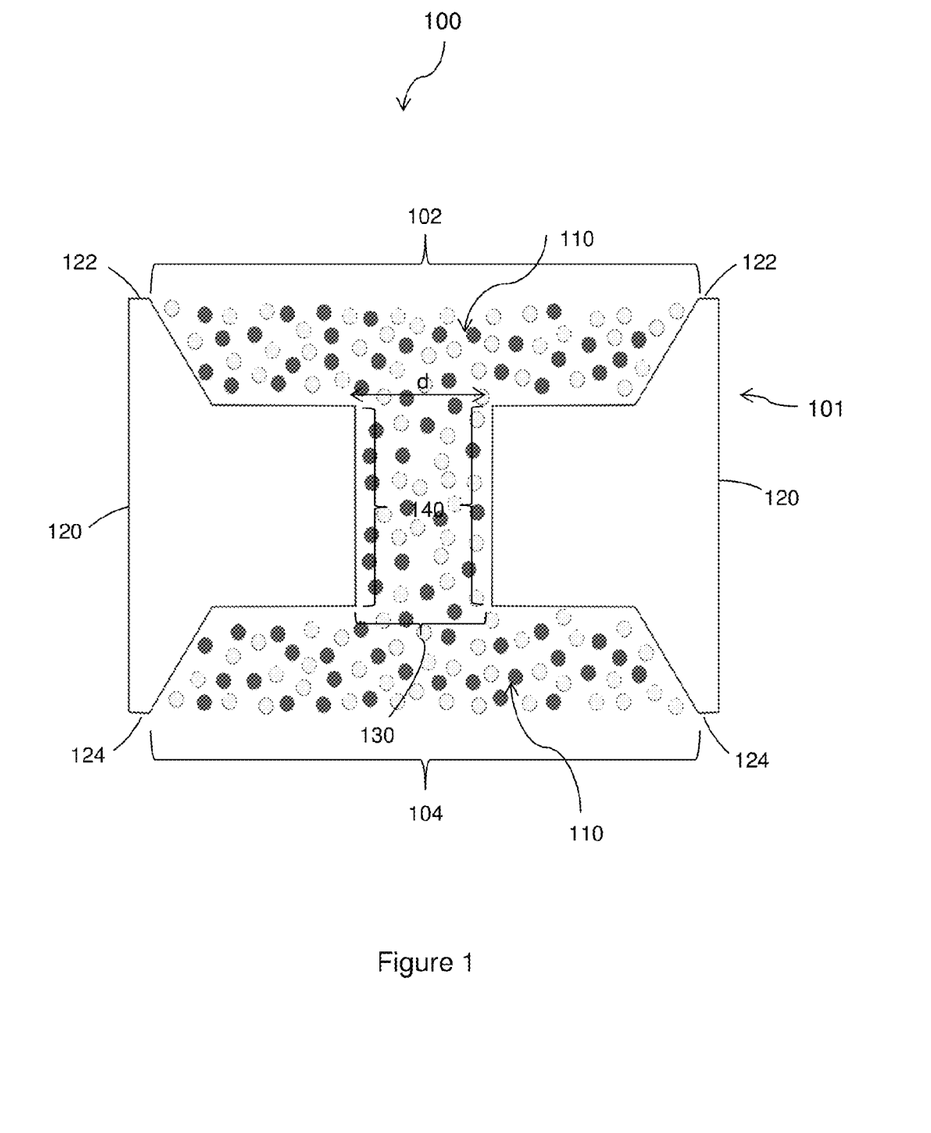
FIG. 1 illustrates a partially cut-away side view of an exemplary embodiment of a nanopore device.

FIG. 1 illustrates a partially cut-away side view of an exemplary embodiment of a nanopore device 100. The nanopore device 100 includes a nanopore structure 101 comprising a substrate 120 having first surface 122 and a second surface 124. The substrate 120 includes a nanochannel 130 extending through the substrate 120 from the first surface 122 to the second surface 124 and separating a cis fluid reservoir 102 and a trans fluid reservoir 104. The nanochannel 130 includes a surface 140 lining the nanochannel 130 through which fluid flows between reservoirs. In operation, the cis and trans fluid reservoirs, 102 and 104, respectively, can be filled with any aqueous electrolyte or charged ion containing solution or buffer solution 110. The nanopore device 100 is but an exemplary embodiment. Other embodiments of the nanopore device 100 can be used.

The buffer solution 110 generally varies and is not intended to be limited. The composition, including the pH, buffers, and ions of the buffer solution 110 depends on the particular application. In one embodiment, the cis fluid reservoir 102 and the trans fluid reservoir 104 can include fluids or buffers that are the same or different.

The nanopore structure 101 can be fabricated from substrates 120 such as chips, disks, blocks, plates and the like. Such substrates 120 can be made from a variety of materials, including but not limited to silicon, including silicon oxide and silicon nitride, hafnium oxide, aluminum oxide, glass, ceramic, germanium, polymers (e.g., polystyrene), and/or gallium arsenide. The substrates 120 can be etched, e.g., chips can be semiconductor chips. The substrate 120 can be a multi-layer substrate. It is not intended for the purpose herein that that any central material in a multi-layer substrate be the same or different than the outer materials. The thickness of the nanopore substrate 120, as well as the thickness of the individual layers within a multi-layer substrate, can generally vary. The particular thickness of the nanopore substrate 120 is not intended to be limited and depends on the particular application. The properties and composition of the surface 140 of the nanochannel 130 depends on the make-up of the substrate 120. Thus, the surface 140 be composed of any of the materials making up the substrate 120.

The nanopore substrate 120 can be fabricated using any suitable fabrication process, including but not limited to, chemical vapor deposition (CVD) methods, plasma enhanced chemical vapor deposition (PECVD) methods, lithographic patterning and etching methods, and epitaxial growth processes. Subsequently, the channel within the nanopore can be fabricated through the substrate by any suitable process, including but not limited to, electron beam drilling, for example TEM, or ion beam drilling. Optionally, the nanopore substrate 120 includes a second, third, or fourth nanochannel for parallel analysis.

The nanochannel 130 diameter d can be tailored to any application. Accordingly, the following diameters are not intended to be limiting. In one embodiment, the nanochannel channel diameter d is about 1 to about 1,000 nm. In another embodiment, the nanochannel diameter d is about 5 to about 50 nm. Yet, in another embodiment, the nanochannel diameter d is about 10 to about 20 nm.

The passage of ions in the buffer 110, molecules, or analytes through the nanochannel 130 can be detected or measured, for example, by measuring the current change from the translocation of ions due to an applied electric field. Any molecules or analytes can be included in the buffer 110. However, any other method of detecting analyte binding can be used, such as the use of embedded electrodes in the substrate 101 to measure electrical signals across the nanopore. Electrical signals can originate from at least one of ionic current, tunneling current, electric field and electric potential.

A coating disposed on a least a portion of the surface 140 of the nanochannel 130 can alter the physical and chemical properties of the nanochannel 130. In addition, a coating can provide a surface exposed functional group that is particular for an analyte of interest. When an analyte binds to a ligand, or specific analyte binding group, on the surface of the coating, a change in the measured current can be detected. These current changes provide chemical, biophysical, and biochemical information about the analyte. Alternatively, when an analyte binding compound is disposed on a surface of the nanochannel, binding of an analyte to the analyte binding group can be electrically detected.

However, conventional coatings have drawbacks because they can be irreversible, which requires individual nanopore structures to be fabricated for specific analyte analysis. Furthermore, cleaning methods to remove coatings are time-consuming and require harsh reagents, which can lead to structural damage to the nanopore itself.

In addition, some conventional coatings utilize large proteins, peptides, or molecules. Thus, these coatings can limit the diameter of nanochannels that can be used.

However, disclosed herein is a versatile and reusable coating that can be disposed onto the surface 140 of a nanochannel 130. In particular, reversible bonds are used to form the coating. Initially, a chemical compound is disposed onto the nanochannel surface 140 to form a monolayer or a coating. The chemical compound includes a reactive functional group that can form a reversible bond. Subsequently, a chemical compound that can simultaneously bind to an analyte of interest and form a reversible bond with the chemical compound is disposed onto the monolayer. Following introduction of an analyte into the nanochannel 130, the analyte binds to an analyte binding group on the nanochannel surface. When analysis is complete, the coating can be reversed, or the reversible bond can be broken, and a new coating can be applied. This method permits re-use and versatility.

Figure 2:
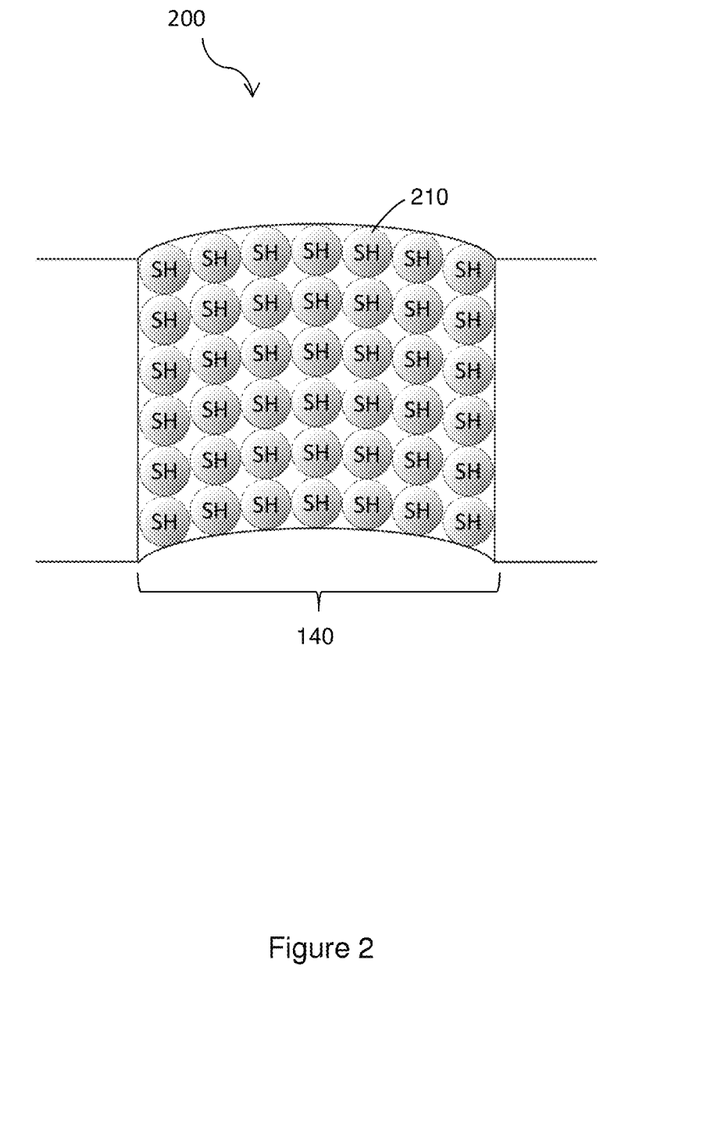
FIG. 2 illustrates a partially cut-away side view of an exemplary embodiment of a coated nanochannel within a nanopore structure.

FIG. 2 illustrates a partially cut-away side view of an exemplary embodiment of a coated nanochannel 200 within a nanopore structure 101 (see FIG. 1). Referring again to FIG. 1, the nanochannel 130 of the nanopore structure 101 can include a monolayer or a coating of a chemical compound 210 comprising a reactive functional group disposed onto a least a portion of the surface 140 of the nanochannel 130. The reactive functional group can be a reactive sulfhydryl group. The cut through the nanochannel 130 shows the surface 140 of the nanochannel 130 coated with the chemical compound 210, with the sulfhydryl groups oriented towards the center of the nanochannel 130. The coated nanochannel 200 is but an exemplary embodiment. Other embodiments of coated nanochannel 200 can be used.

In one embodiment, the chemical compound 210 includes any reactive functional group, molecule, or biomolecule that can form a reversible bond with another functional group. Suitable examples of reactive groups capable of forming a reversible bond include a protein, a peptide, an antibody, a small molecule, a polymer, a lipid, a polynucleotide, a DNA strand, a carbohydrate, or any combination thereof. Other non-limiting examples of suitable reactive groups include an acrylate group, an acyl halide group, an amide group, an amine group, a carboxylate group, a carboxylate thiol group, an ester group, an ether group, a hydroxamic acid group, a hydroxyl group, a methacrylate group, a nitrate group, a nitrile group, a phosphate group, a phosphine group, a phosphonic acid group, a silane group, a sulfate group, a sulfide group, a sulfite group, a sulfhydryl group, a thiolate group, an alkene group, an alkyne group, an azide group, an acetal group, an aldehyde group, a diene group, an anhydride, or any combination thereof.

In another embodiment, the chemical compound 210 forming the monolayer has a first reactive sulfhydryl group and substantially covers the surface 140 of the nanochannel 130. The analyte binding compound disposed on top of the monolayer can then include a second sulfhydryl group, which can form a reversible disulfide bond.

In another embodiment, the coating can substantially cover all or a portion of the surface 140 of the nanochannel 130. The chemical compound 210 can form a monolayer or a coating on the surface 140 of the nanochannel 130. Multiple layers can also be used.

The coating or monolayer can be formed by initially disposing the chemical compound 210 onto the nanochannel surface 140 at any point during the nanopore structure 101 fabrication process. In addition to reactive groups forming the reversible bond, which are substantially oriented away from the surface 140 and/or towards the center of the nanochannel 130, the chemical compound 210 includes a functional group that interacts with the surface 140. The functional group can have any affinity for the surface 140 of the nanochannel 130 that enables the functional group to bind to or form a contact product with the surface 140.

The functional group of the chemical compound 210 forming a contact product with the surface 140 generally varies and is not intended to be limited. The chosen functional group depends on the surface properties of the substrate 120. Suitable functional groups include, but are not limited to, an acrylate group, an acyl halide group, an amide group, an amine group, a carboxylate group, a carboxylate thiol group, an ester group, an ether group, a hydroxamic acid group, a hydroxyl group, a methacrylate group, a nitrate group, a nitrile group, a phosphate group, a phosphine group, a phosphonic acid group, a silane group, a sulfate group, a sulfide group, a sulfite group, a thiolate group, an alkene group, an alkyne group, an azide group, an acetal group, an aldehyde group, a diene group, an anhydride, or any combination thereof.

In an exemplary embodiment, the surface 140 of the nanochannel 130 is relatively basic, for example comprising silicon nitride, hafnium oxide, or aluminum oxide. Monolayers of a bi-functional chemical compound 210 bearing a phosphonic acid group or a hydroxamic acid group are then disposed onto the surface 140. The result is a coating of a chemical compound 210 that can form a reversible and severable bond with different analyte binding compounds.

The functional group forming the contact product with the nanochannel surface and the reactive functional group forming the reversible bond of the chemical compound 210 can be directly linked or indirectly linked by using a linker molecule or group. The optional linker can be any chemical compound, polymer, or biopolymer. Non-limiting examples of suitable linkers include variable length hydrocarbons, peptides, biopolymers, synthetic polymers (for example polyethylene glycol (PEG)), or any combination thereof. The length of the linker can be adjusted to any desired length. Optionally, the linker can be branched.

The initial monolayer on the surface 140 of the nanochannel 130 provides a versatile nanopore structure 101 because subsequently, any compound having at least another reactive group linked to an analyte binding group can be reversibly disposed onto the surface 140 of the nanochannel 130. The versatility of the coating stems from the ability to break and reform the reversible bond with another chemical compound having a functionality specific for binding or detecting a different analyte. Thus, the coating can be reused.

In an exemplary embodiment, a nanopore structure comprises a substrate comprising a nanochannel and a monolayer of a chemical compound disposed onto at least a portion of a surface of the nanochannel, wherein the chemical compound forms a reversible bond with at least one analyte binding compound introduced into the nanochannel. The at least one analyte binding compound can comprise a functional group forming the reversible bond, and the reversible bond can be selectively severed. The ability to selectively sever the reversible bond permits reuse and versatility to detect many types of analytes.

In particular, the disclosed coating offers greater versatility compared to conventional nanopore structures and devices without such coatings by permitting the selective binding of proteins or other molecules of interest from a mixture of molecules. This type of coating can be used in drug discovery applications, where many potential drugs (ligands or analytes) are screened against a particular target, or analyte binding group. Furthermore, these coatings can be extended to diagnostic applications.

The coating method disclosed also permits reuse of nanopore devices. Because surface functionalized nanochannels can be irreversible, or difficult to reverse, new nanochannels must be used each time a new nanochannel surface functionalization is required, e.g., every time a new ligand or analyte binding group is required. However, using reversible bonds to reversibly bind functionalization molecules to the nanochannel surface increases the versatility of nanochannels by permitting the easy removal and re-coating of the nanochannel surface.

Using disulfide bonds as a reversible coating provides greater flexibility to make the ligand, or analyte binding group/receptor, a part of the reversible functional surface, as opposed to the surface itself. Thus, the size of the moiety coating the channel can be controlled.

In applications where it is necessary to maximize the nanochannel blockage upon binding of proteins or other analytes, it is advantageous to have the larger molecule that binds to the coating, such as a protein, incorporating the smaller molecule, such as the ligand. This will result in larger electrical signal changes. In particular, larger molecules exclude a larger volume of fluid in the nanopore, thereby increasing the electrical signal upon entering the pore. This increases the signal and improves the sensitivity of the device. In addition, using reversible bonds such as disulfide bonds in the coating means that the nanochannel size does not have to be compromised.

Another advantage of the disclosed reusable coating is that small ligands do not substantially decrease the pore size. In contrast to conventional coatings, for example coatings including large histidine-tagged antibodies, disulfide containing coatings, or containing utilizing small functional groups or bonds, provide a coating that does not have size restrictions.

Further, the coating is easily removed using chemical severing agents, such as reducing agents when the bond is a disulfide bond, and does not require harsh reagents for removal. Thus, the nanochannel coating is more versatile, and thus the technique is more robust in terms of throughput.

When the reversible bond is a disulfide bond, chemical compounds of the coating only need to contain a small, functional sulfhydryl group, not larger peptide/protein tag. Tagging of chemical compounds, particularly proteins, used in coatings can have an impact on the function of the chemical compound. Removing the need for a tag in the chemical compound of the coating can make use of systems that may not have been accessible through conventional methods of protein tagging.

Figure 3:
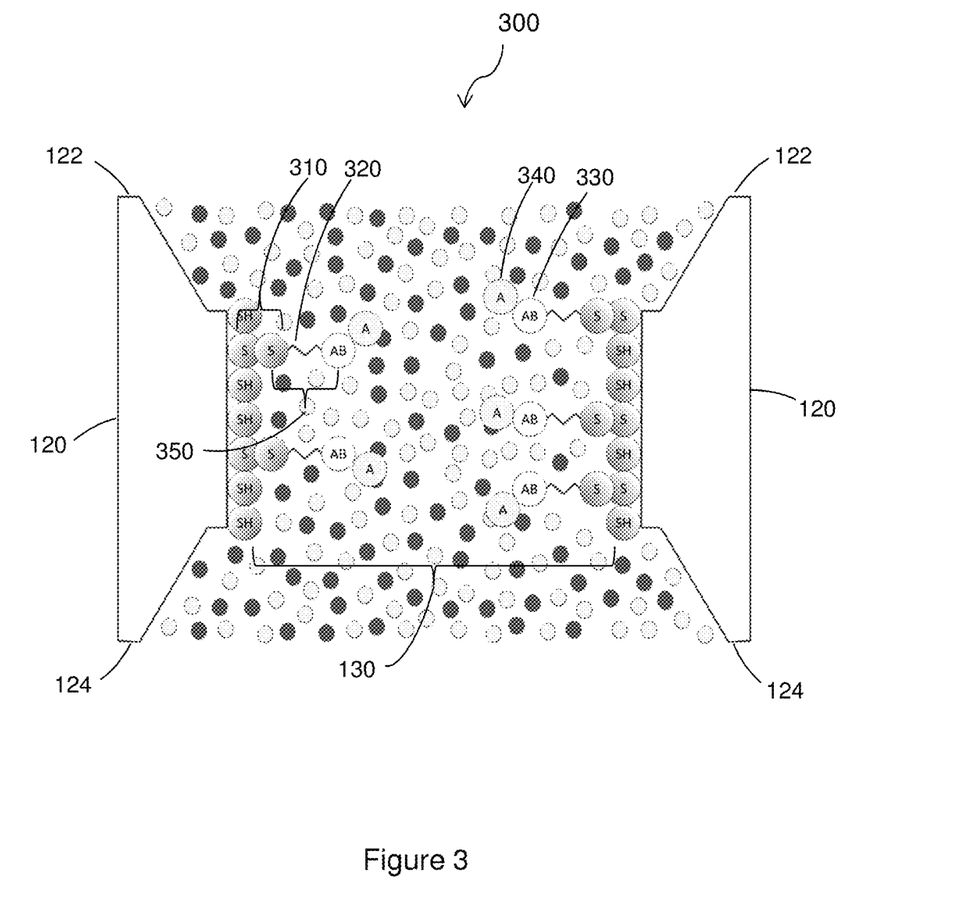
FIG. 3 illustrates a partially cut-away side view of an exemplary embodiment of a nanopore structure with a reusable disulfide coating.

FIG. 3 illustrates a partially cut-away side view of an exemplary embodiment of a nanopore structure 300 including a disulfide-containing reusable coating. Following depositing a monolayer of a chemical compound 210 comprising a first sulfhydryl group onto at least a portion of the surface 140 of the nanochannel 130, an analyte binding compound 350 comprising a second sulfhydryl group forming a reversible disulfide bond 310 with the first sulfhydryl group is disposed onto the monolayer. Further, the analyte binding compound 350 comprises an analyte binding group 330 that interacts with or forms a contact product with an analyte 340 of interest. Although the analyte binding group 330 can be linked directly to the second sulfhydryl group, optionally, the analyte binding compound 350 includes a linker 320 connecting the analyte binding group 330 to the second sulfhydryl group forming the disulfide bond 310. The nanopore structure 300 of FIG. 3 is but an exemplary embodiment. Other embodiments of nanopore structure 300 can be used.

The reversible bond between the analyte binding compound 350 and the chemical compound 210 disposed on the surface 140 of the nanochannel 130 can be formed by filling either one or both of the cis and trans fluid reservoirs, 102 and 103, respectively, with the analyte binding compound 350 in an appropriate solvent, e.g., water, along with an oxidizing agent. When the analyte binding compound 350 enters the nanochannel 130, the oxidizing agent can aid in forming links or bonds between the analyte binding compound 350 molecules to the chemical compound 210 coating. Analyte binding compounds 350 that react with each other to form homo-coupling products can be washed away with excess water, buffer, or solvent. Analyte binding compounds 350 attached to the chemical compound 210 of the coating will remain attached to the surface 140 via the newly formed reversible bond 310. The end result is a nanochannel 130 containing an analyte binding group 330 that can bind to another protein or analyte 340 of interest, but is reversibly attached to the wall or surface 140 of the nanochannel 130.

In one exemplary embodiment, a ligand (analyte binding group 330) containing neurotensin, a small neuropeptide widely distributed in the central nervous system, could be attached to a moiety containing a sulfhydryl group. This ligand could be used to coat the nanochannel 130 functionalized with thiol groups capable of forming disulfide bonds. Neurotensin binds to neurotensin receptor 1 (NTS1) with very high affinity, thus the binding of NTS1 to neurotensin can be measured in a nanopore device using this coating. Once binding and/or translocation has been measured, the neurotensin/ligand coating can be removed by introducing a reducing agent into the nanochannel 130, before being recharged with any other potential ligand that is of interest.

When the bond is a reversible disulfide bond, an oxidizing agent can be used to promote formation of the disulfide bond 310. Suitable non-limiting examples of oxidizing agents include hydrogen peroxide, perborate or bromate salts, for example sodium perborate and sodium bromate, or any combination thereof. In one embodiment, the disulfide bond 310 is formed in the absence of an oxidizing agent. When present, the oxidizing agent is present in an amount effective to promote disulfide bond 310 formations.

The analyte 340 can be a compound, molecule, substance or chemical constituent that is undergoing analysis or sought to be detected. It is not intended that the present disclosure be limited to a particular analyte. Representative analytes include ions, peptides, proteins, antibodies, carbohydrates, polynucleotides, DNA strands, polymers, lipids, ions, metals, or any combination thereof.

The analyte binding group 330 can be any functional group or ligand that can interact with, form a contact product with, or bind an analyte 340. As the analyte 340 is variable, the following examples of analyte binding groups 330 are not intended to be limiting. Suitable examples of analyte binding groups 330 include small chemical compounds, molecules, and biochemical compounds, e.g., peptides, proteins, antibodies, carbohydrates, polynucleotides, DNA strands, polymers, lipids, ions, metals, or any combination thereof.

Figure 4:
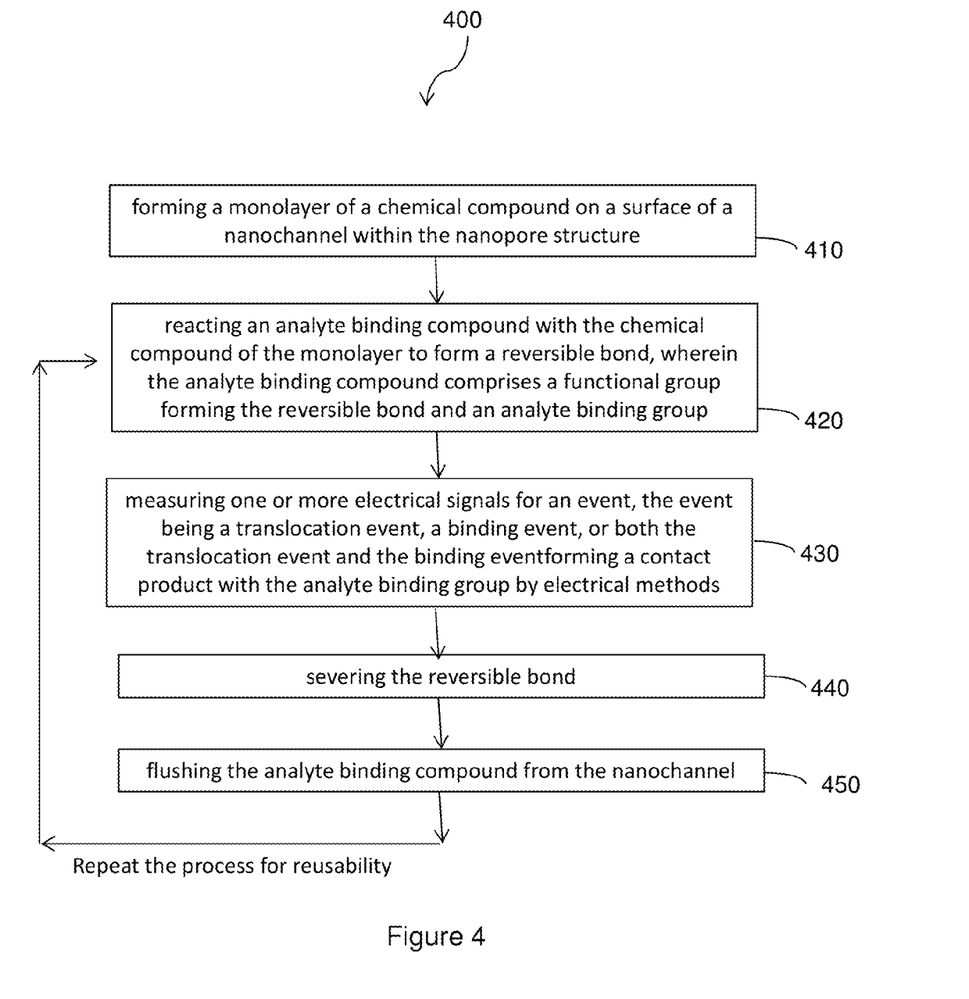
FIG. 4 illustrates a block diagram of an exemplary embodiment of a method for using a reversible coating in a nanopore structure.

FIG. 4 illustrates a block diagram of an exemplary method 400 for using a reusable coating within a nanopore structure 101. In block 410, the method 400 includes forming a monolayer of a chemical compound on a surface of a nanochannel within the nanopore structure. In block 420, an analyte binding compound is reacted with the chemical compound of the monolayer to form a reversible bond. The analyte binding compound comprises a functional group forming the reversible bond and an analyte binding group. In block 430, one or more electrical signals are measured for an event, the event being a translocation event, a binding event, or both the translocation event and the binding event. A translocation event can be the analyte initially binding to the analyte binding group (a binding event) and then un-binding and leaving the nanopore. In block 440, the reversible bond is severed. In block 450, the analyte binding compound is flushed from the nanochannel. Subsequently, the method 400 can be repeated for reusability, for example by starting with block 420. The method 400 is but an exemplary embodiment. Other embodiments of the method 400 can be used.

During the method of 400, the different solutions can be manually or automatically introduced into cis chamber 102 for filling of the nanodevice. The various solutions can include electrolytes, buffers, reducing agents, severing agents, analytes, or any combination thereof. Automatic entry can be controlled via programmable electronically controlled gates to other chambers that hold the individual solutions not included in the device.

Figure 5:
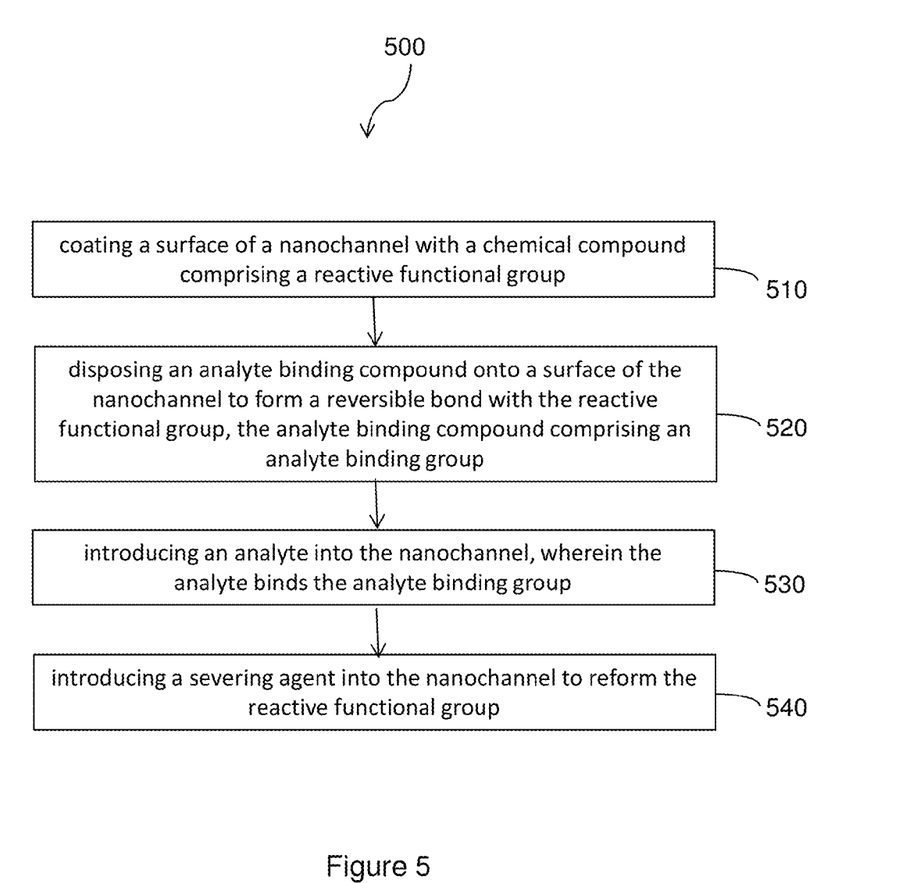
FIG. 5 illustrates a block diagram of an exemplary embodiment of a method for making a reusable nanopore structure having a reversibly bound analyte binding group.

FIG. 5 illustrates a block diagram of an exemplary method 500 for making a reversible analyte-binding coating in a nanopore structure. In block 510, the surface of the nanochannel is coated with a chemical compound comprising a reactive functional group. In block 520, an analyte binding compound is disposed onto a surface of the nanochannel to form a reversible bond with the reactive functional group. The surface of the nanochannel can be coated with the chemical compound by introducing a fluid comprising the chemical compound into the nanochannel. The analyte binding compound includes an analyte binding group. In block 530, an analyte is introduced into the nanochannel, and the analyte forms a contact product with, or binds to, the analyte binding group. In block 540, a severing agent is introduced into the nanochannel to break the reversible bond and reform the reactive functional group. Further, introducing the severing agent into the nanochannel can simultaneously break the reversible bond and remove the analyte binding compound from the surface of the nanochannel. Subsequently, the analyte binding compound can be flushed from the nanochannel. The method 500 is but an exemplary embodiment. Other embodiments of method 500 can be used.

Various methods of selectively severing the reversible bond can be used. Non-limiting examples of suitable methods include chemical methods, temperature methods, electrical methods, pH methods, or any combination thereof. In particular, chemical reagents (severing agents) can be introduced into the nano channel, the pH of the nanochannel environment or buffers within the nanochannel can be altered, the temperature of the nanochannel environment can be increased or decreased, or electrical voltage and current changes can be used.

When the reversible bond is a disulfide bond, reducing agent can be used to sever the reversible bond. The reducing agent breaks the reversible disulfide bond and removes the analyte binding compound from the surface of the nanochannel. Subsequently, a second analyte binding compound can be disposed onto the surface of the nanochannel to re-form the reversible disulfide bond with the reactive sulfhydryl group, with the analyte binding compound comprising a different analyte binding group.

Non-limiting exemplary reducing agents include thiol-containing reducing agents and bisulfite ion-containing reducing agents. Exemplary thiol-containing reducing agents include mercaptocarboxylic acids, their alkali metal and ammonium salts, their esters and glyceryl esters, and mixtures thereof. Examples of these reducing agents include thioglycolic acid, thiolactic acid, 3-mercaptopropionic acid, and the like. Suitable alkali metal salts of these acids include sodium or potassium salts, for example sodium thioglycolate. Ammonium salts, for example ammonium thioglycolate, can also be used, and include salts prepared from these acids and ammonia, mono-, di-, or tri-ethanolamine and mono-, di- or tri-iso-propanolamine. Examples of mercaptocarboxylic acid esters include glyceryl thioglycolate. Non-limiting exemplary bisulfite ion-containing reducing agents include alkali metal and ammonium bisulfite.

Figure 6:
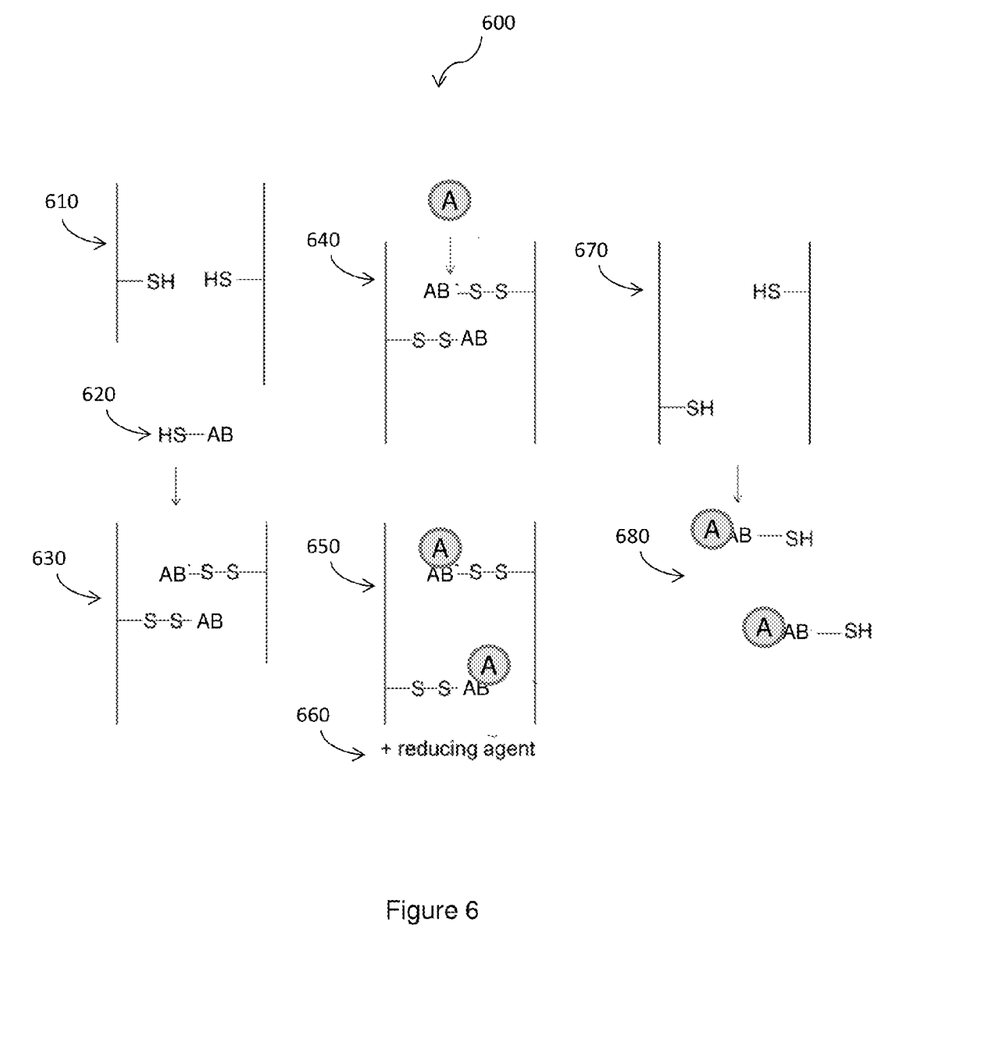
FIG. 6 illustrates a schematic of an exemplary embodiment of a method for making and using a reusable coating in a nanopore structure.

FIG. 6 illustrates an exemplary embodiment of a method 600 for using disulfide bonds to make a reversible coating within a nanopore structure. In 610, the surface of a nanochannel is coated, forming a monolayer, with a chemical compound or a protein comprising a reactive sulfhydryl group. The sulfhydryl group is oriented away from the nanochannel surface and towards the interior of the channel, or away from the surface of the nanochannel. In 620, an analyte binding compound having a second free sulfhydryl group and an analyte binding group is introduced into the nanochannel. In 630, a reversible disulfide bond is formed between the sulfhydryl groups of the analyte binding compound and the monolayer on the nanochannel surface. In 640, an analyte of interest is introduced into the nanochannel. In 650, the analyte binds to the analyte binding group lining the nanochannel. In the presence of an applied electric field, a change in current output can be observed, indicating a binding event. In 660, a reducing agent is introduced into the nanochannel. In 670, the reducing agent breaks the disulfide bonds, regenerating the reactive sulfhydryl groups of the initial coating. In 680, the analyte binding compound and the bound analyte are removed from the nano channel. Following breaking of the disulfide bonds, another analyte binding compound specific for any other analyte of interest can be introduced into the nanochannel and the nanopore can be reused. The method 600 is but an exemplary embodiment. Other embodiments of the method 600 can be used.

During operation of a nanopore device, the nanopore structure should allow for a sufficiently large ionic current under an applied electric field to provide for adequate measurement of current fluctuations. Current fluctuations are induced by binding and un-binding of an analyte to a ligand bound to a coating of the nanochannel. The current has a current path defined by the nanochannel within the nanopore structure. These current fluctuations provide chemical and biochemical information about the analyte.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method for using a re-usable coating within a nanopore structure, the method comprising:
    forming a monolayer on a silicon nitride surface of a nanochannel within the nanopore structure, the monolayer comprising a bifunctional chemical compound comprising a hydroxamic acid group or a phosphonic acid group reactive with the silicon nitride surface and a first sulfhydryl group that extends from a surface of the monolayer;
    reacting an analyte binding compound in the presence of an oxidizing agent with the monolayer to form a reversible disulfide bond, the analyte binding compound comprising a second sulfhydryl group linked to an analyte binding group via a linker group, the second sulfhydryl group forming the reversible disulfide bond with the first sulfhydryl group;
    introducing an analyte into the nanochannel;
    measuring one or more electrical signals for an event, the event being a translocation event, a binding event, or both the translocation event and the binding event;
    severing the reversible disulfide bond to reform the first sulfhydryl group in the monolayer;
    flushing the analyte binding compound from the nanochannel; and
    re-using the monolayer on the surface of the nanochannel by reacting another analyte binding compound comprising a terminal sulfhydryl group with the first sulfhydryl group of the monolayer.

2. The method of claim 1, wherein the analyte binding group is a protein, a peptide, an antibody, a small molecule, a polymer, a lipid, a polynucleotide, a DNA strand, a carbohydrate, or any combination thereof.

3. A method for making a reversible analyte-binding coating in a nanopore structure, the method comprising:
    coating a surface of a nanochannel with a monolayer, the surface of the nanochannel comprising silicon nitride, and the monolayer comprising a bifunctional chemical compound comprising a hydroxamic acid group or a phosphonic acid group reactive with the silicon nitride surface and a first sulfhydryl group extending from a surface of the monolayer;
    disposing an analyte binding compound in the presence of an oxidizing agent onto a surface of the monolayer to form a reversible disulfide bond with the monolayer, the analyte binding compound comprising a second sulfhydryl group linked to an analyte binding group, the second sulfhydryl group forming the reversible disulfide bond with the first sulfhydryl group;
    introducing an analyte into the nanochannel, the analyte binding to the analyte binding group; and
    introducing a severing agent into the nanochannel to break the reversible disulfide bond.

4. The method of claim 3, wherein the severing agent is a thiol-containing reducing agent, a bisulfite ion-containing reducing agent, or any combination thereof.

5. The method of claim 3, wherein introducing the severing agent into the nanochannel removes the analyte binding compound from the surface of the nanochannel.

6. The method of claim 3, further comprising disposing a second analyte binding compound onto the surface of the nanochannel to re-form the reversible disulfide bond, the second analyte binding compound comprising a different analyte binding group.

* * * * *